US011363954B2

United States Patent
Horesh et al.

(10) Patent No.: US 11,363,954 B2
(45) Date of Patent: Jun. 21, 2022

(54) FLUORESCENT IMAGER WITH LIMITED VARIABLE GAIN

(71) Applicant: Visionsense LTD., Petach Tikva (IL)

(72) Inventors: Nadav Horesh, Ramat Raziel (IL); Alex Chanin, Holland, PA (US); Ofer Braude, Ramat Gan (IL)

(73) Assignee: Visionsense LTD., Petach Tikva (IL)

( * ) Notice: Subject to any disclaimer, the term of this patent is extended or adjusted under 35 U.S.C. 154(b) by 415 days.

(21) Appl. No.: 16/150,473

(22) Filed: Oct. 3, 2018

(65) Prior Publication Data
US 2019/0099081 A1 Apr. 4, 2019

(51) Int. Cl.
*A61B 5/00* (2006.01)
*A61B 1/04* (2006.01)
*A61B 5/1455* (2006.01)
*H04N 5/52* (2006.01)
*A61B 5/0275* (2006.01)
*A61B 5/026* (2006.01)

(52) U.S. Cl.
CPC ............ *A61B 5/0071* (2013.01); *A61B 1/043* (2013.01); *A61B 5/0059* (2013.01); *A61B 5/14556* (2013.01); *A61B 5/7225* (2013.01); *H04N 5/52* (2013.01); *A61B 5/0261* (2013.01); *A61B 5/0275* (2013.01); *A61B 2505/05* (2013.01)

(58) Field of Classification Search
CPC ... A61B 5/0071; A61B 1/043; A61B 5/14556; A61B 5/0059; A61B 5/7225; A61B 5/0261; G01N 29/4463; G01N 2021/933; H03G 2201/20; G04B 10/2942; G10K 2210/3056; G10K 2210/3213; G01D 5/2448; H04N 5/52
See application file for complete search history.

(56) References Cited

U.S. PATENT DOCUMENTS

| 6,059,720 A * | 5/2000 | Furusawa .......... A61B 1/00186 348/E5.041 |
| 7,043,291 B2 | 5/2006 | Sendai |
| 7,589,316 B2 | 9/2009 | Dunki-Jacobs |
| 7,635,330 B2 * | 12/2009 | Kang .................. A61B 1/00009 600/109 |
| 2002/0177780 A1 * | 11/2002 | Sendai ............... A61B 1/00186 600/476 |

(Continued)

*Primary Examiner* — Carolyn A Pehlke
*Assistant Examiner* — Johnathan Maynard
(74) *Attorney, Agent, or Firm* — Carter, DeLuca & Farrell LLP

(57) ABSTRACT

A device and method for fluorescent imaging may include an imaging unit including a fluorescent camera with an optical detector that is configured to acquire a fluorescent image of a fluorescing sample, the image including raw pixel values. A user interface may display an image formed from display image pixels derived from the raw image pixels. A distance sensor may measure a distance to the fluorescing sample. A distance between the optical detector and fluorescing sample may be determined from the measured distance. A processing unit may obtain a gain value, match the determined distance to a distance value associated a respective gain range, and impose limits of the gain values range onto the gain value, to determine a limited gain value. The limited gain value may be applied to the raw image pixels, thereby deriving display image pixels.

20 Claims, 4 Drawing Sheets

(56) References Cited

U.S. PATENT DOCUMENTS

| | | | |
|---|---|---|---|
| 2006/0025692 A1* | 2/2006 | Ishihara | A61B 1/00096 600/478 |
| 2008/0015446 A1* | 1/2008 | Mahmood | A61B 1/045 600/476 |
| 2008/0177140 A1* | 7/2008 | Cline | A61B 1/05 600/112 |
| 2010/0053366 A1* | 3/2010 | Mizuno | H04N 5/144 348/E9.051 |
| 2010/0245551 A1* | 9/2010 | Morita | G06T 5/007 348/E7.085 |

* cited by examiner

FLUORESCENT IMAGER WITH LIMITED VARIABLE GAIN

CROSS-REFERENCE TO RELATED APPLICATIONS

This application claims benefit of prior Israeli Patent Application No. 254896, filed Oct. 3, 2017, which is hereby incorporated by reference.

FIELD OF THE DISCLOSED TECHNIQUE

The disclosed technique relates to medical imaging in general, and fluorescent medical imaging in particular.

BACKGROUND OF THE DISCLOSED TECHNIQUE

Fluorescence imaging is a known in the art technique for medical diagnostics. To image tissue in vivo, a fluorescent dye or stain is added to the blood flowing within the tissue. The fluorescent molecules of the dye, or 'fluorophores', bind with the blood cells, fluorescently labelling them. During surgery, the tissue is illuminated with a light source selected to excite the fluorophores, causing them to emit fluorescent light. A fluorescent microscope collects the emitted light using optical filters selected to match the emission spectrum of the fluorophores. The filtered light is detected by an electronic imaging sensor, such as a CMOS or CCD camera, and the resulting fluorescent image is displayed for further analysis. The fluorescent microscope may acquire multiple images over a given timespan to produce an in vivo video of the blood flow in real time. In this manner, the internal blood flow through the tissue may be imaged during surgery, and tissue perfusion and vessel patency may be evaluated.

Some fluorescent dyes used in medical imaging have a relatively low quantum efficiency. For example, IndoCyanine Green (ICG) has a quantum efficiency of approximately 1%, producing a weak fluorescence signal even when excited by a strong excitation source. Additionally, when the fluorophores are imaged through tissue, both the excitation and the fluorescence light are strongly attenuated by the tissue in a non-linear manner, depending on the thickness and composition of the skin. To compensate for this attenuation, a gain is added to the raw video signal acquired by the sensor. A suitable gain might amplify the detected signal such that the resulting image is bright enough to be displayed and evaluated without saturating the image pixels.

A known in the art technique for addressing signal attenuation calls for adding a fixed gain to the raw video signal, such that the gain remains unchanged throughout the image acquisition process. This gain may be preconfigured as a system parameter, or alternatively may be set by the user. Adding the fixed gain requires that the sensor be positioned at an appropriate distance from the fluorescent target. However, this approach does not account for the fact that the fluorescence signal strength may vary considerably due to patient tissue parameters. For example, imaging blood with fluorescent dye flowing through the skin of a relatively young person will produce a much weaker signal than imaging blood with fluorescent die flowing through the skin of an older person due to the reduction in skin thickness associated with aging. Thus, maintaining the same distance between sensor and skin surface for both younger and older patients will produce significantly different brightness images and may leading to misleading diagnoses.

Another known in the art technique for addressing signal attenuation automatically calls for adjusting the gain of the raw signal based on the pixel values of the resulting image. According to this technique, an Automatic Gain Control (AGC) circuit or algorithm measures the brightness of the displayed pixels, and uses the brightness values to compute a corrective gain, which is then applied to the raw signal data. This approach does not require any user interaction, and is commonly used for perfusion imaging, where the fluorescent dye is bound to blood proteins. As the blood enters the vasculature of interest, the dye fluoresces, allowing the blood in-flow to be imaged and evaluated. However, since this system automatically adjusts the gain of the raw signal from the sensor, it will automatically amplify weak signals in order to produce an image within a target pixel value range. This approach may amplify noise rather than the true fluorescence signal. Additionally, when evaluating blood out-flow, automatic gain adjustment may lead to inaccurate, and even false conclusions. For blood out-flow evaluation, the fluorescent image of the vasculature of interest should become dimmer over time as blood tagged with the fluorescent dye is cleared from the vasculature of interest. Eventually, the image should show only a very weak residual fluorescence. However, in a system with automatic gain control, the weakening fluorescent signal produced by blood out-flow will increasingly amplified by the automatic gain correction. The resulting image will be displayed with relatively constant brightness, risking an incorrect clinical diagnosis.

U.S. Pat. No. 7,589,316 B2 filed January 2007, issued September 2009, discloses adjusting the gain of a scanning beam imaging assembly directed at a reflective surface, based on the reflective coefficient of the respective reflective surface.

U.S. Pat. No. 7,043,291 B2 filed May 2002, and issued May 2006, discloses a fluorescence image display apparatus that computes gain based on a statistical formula using data from multiple fluorescent images.

U.S. Pat. No. 7,635,330 B2 file March 2005, and issued December 2009 discloses adjusting the gain applied to a fluorescent endoscope according to the ratio between the reflected excitation light and the fluorescent light.

U.S. Pat. No. 6,059,720 filed mar 1998, and issued May 2000 discloses amplifying an image captured by an endoscope.

SUMMARY OF THE PRESENT DISCLOSED TECHNIQUE

It is an object of the disclosed technique to provide a novel method and system for adjusting the target brightness of a fluorescent image of tissue, acquired using a fluorescence imaging device.

In accordance with the disclosed technique, there is thus provided a fluorescent imaging device, comprising: an imaging unit, comprising: a fluorescent camera comprising an optical detector that is configured to acquire at least one fluorescent image of a fluorescing sample, wherein the at least one fluorescent image comprises multiple raw pixel values, and a user interface configured to display an image defined by multiple display image pixels, the multiple display image pixels derived from the multiple raw image pixels; a processing unit configured to provide the multiple display image pixels to the user interface; and a distance sensor configured to measure a distance to the fluorescing sample and provide the measured distance to the processing unit, wherein the processing unit is configured to determine a distance between the optical detector and the fluorescing sample from the measured distance, match the determined distance to one of a plurality of distance values, each associated with a respective gain values range, obtain the respective gain values range stored in association with the matched distance value, and apply a gain value within the gain values range to the multiple raw image pixels, thereby deriving the multiple display image pixels.

In some embodiments, the fluorescent imaging device further comprises a memory unit configured to store the plurality of distance ranges and the respective associated gain values ranges.

In some embodiments, the processing unit is further configured to apply a smoothing technique to select one of multiple gain values ranges, each of the multiple gain values range associated with the determined distance.

There is further provided, in accordance with an embodiment, a method for applying a limited variable gain to a fluorescent image, comprising: associating between each of a plurality of distance values and a respective gain values range; acquiring, by an optical detector, at least one fluorescent image of a fluorescing sample, wherein the at least one fluorescent image comprises multiple raw pixel values; determining a distance between the optical detector and the fluorescing sample; obtaining the respective gain values range associated with the determined distance; applying a gain value from the obtained gain values range to the multiple raw image pixels, thereby deriving multiple display image pixels; and storing the multiple display image pixels.

In some embodiments, the method further comprises matching the determined distance to one of the plurality of distance values, and obtaining the respective gain values range in accordance with the matched one of the plurality of distance values.

In some embodiments, the method further comprises measuring a distance from the fluorescing sample, and applying the measured distance to determine the distance between the optical detector and the fluorescing sample.

In some embodiments, the method further comprises applying a smoothing technique to select one of multiple gain values ranges, each of the multiple gain values range associated with the determined distance.

There is further provided, in accordance with an embodiment, a computer program product comprising a non-transitory computer-readable storage medium having program code embodied thereon, the program code executable by at least one hardware processor to: determine a distance between an optical detector and a fluorescing sample; match the determined distance to one of a plurality of distance values, each of the plurality of distance values associated with a respective gain values range; obtain the respective gain values range in accordance with the matched one of the plurality of distance values; apply a gain value from the obtained gain values range to multiple raw image pixels of at least one fluorescent image of a fluorescing sample, the fluorescent image detected by the optical detector, thereby deriving multiple display image pixels, the multiple display image pixels defining an image; and store the multiple display image pixels.

In some embodiments, the program code is further executable to match the determined distance to one of the plurality of distance values, and obtaining the respective gain values range in accordance with the matched one of the plurality of distance values.

In some embodiments, the program code is further executable to apply a measured distance from the fluorescing sample to determine said distance between the optical detector and the fluorescing sample.

In some embodiments, the program code is further executable to apply a smoothing technique to select one of multiple gain values ranges, each of the multiple gain values range associated with the determined distance.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a system and method for adjusting the target brightness of a fluorescent image of tissue, acquired using a fluorescence imaging device. In addition to an optical detector for acquiring the fluorescent image, the disclosed device includes a distance sensor for measuring the distance between the optical detector and the fluorescent tissue. The gain applied to the raw fluorescent signal detected by the fluorescent imaging device is either increased or decreased, according to this determined distance. In this manner, the brightness of the image pixels, and thus the brightness of the displayed fluorescent image, is adjusted in accordance with the determined distance. The gain is determined in accordance with a limited variable gain algorithm that imposes predefined maximum and minimum gain values in accordance with respective minimum and maximum distance ranges. In this manner, the chance of applying too much gain, resulting in over-amplification of the signal, or too little gain, resulting in too dim an image, is significantly reduced.

Figure 1A:
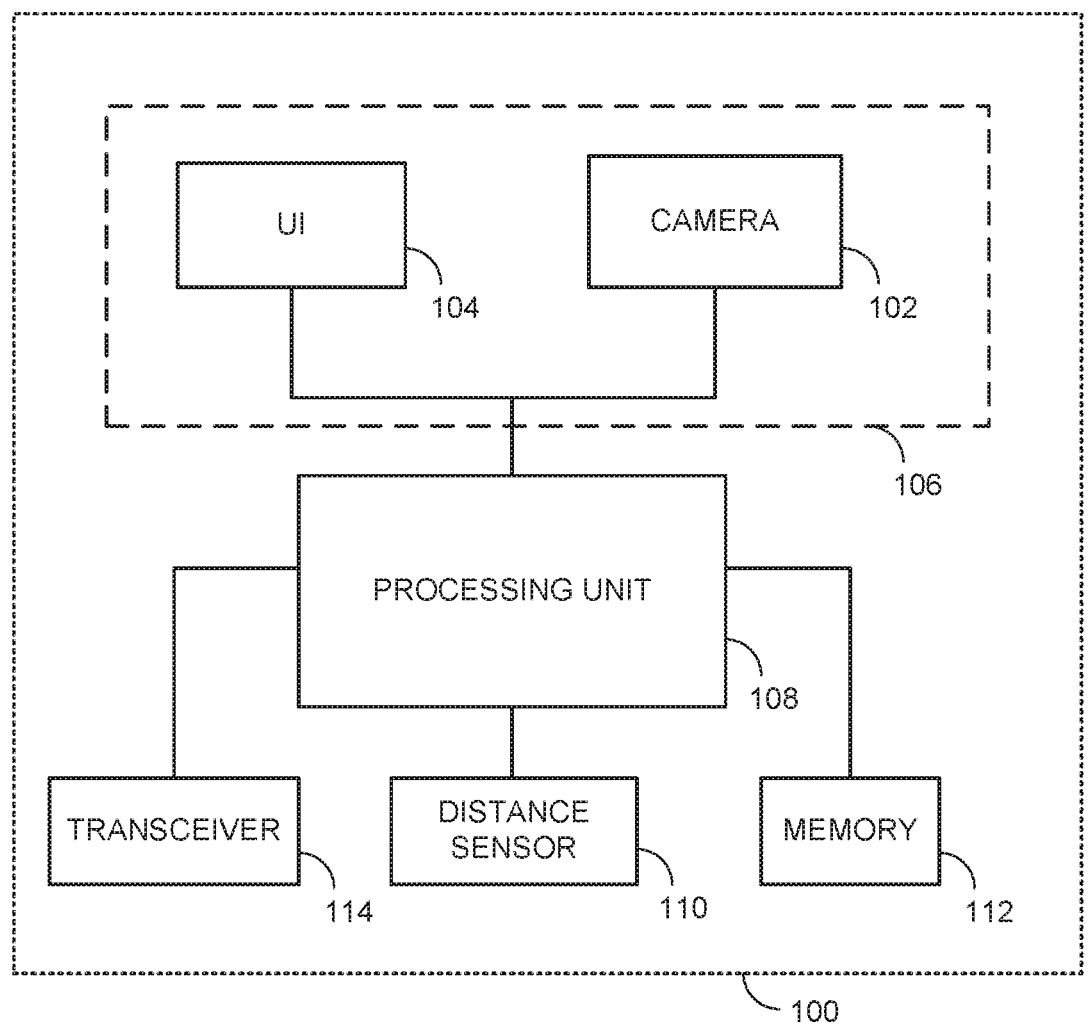
FIGS. 1A-1B are schematic block diagrams of a fluorescent imager with limited variable gain, in accordance with an embodiment of the disclosed techniques.
Figure 1B:
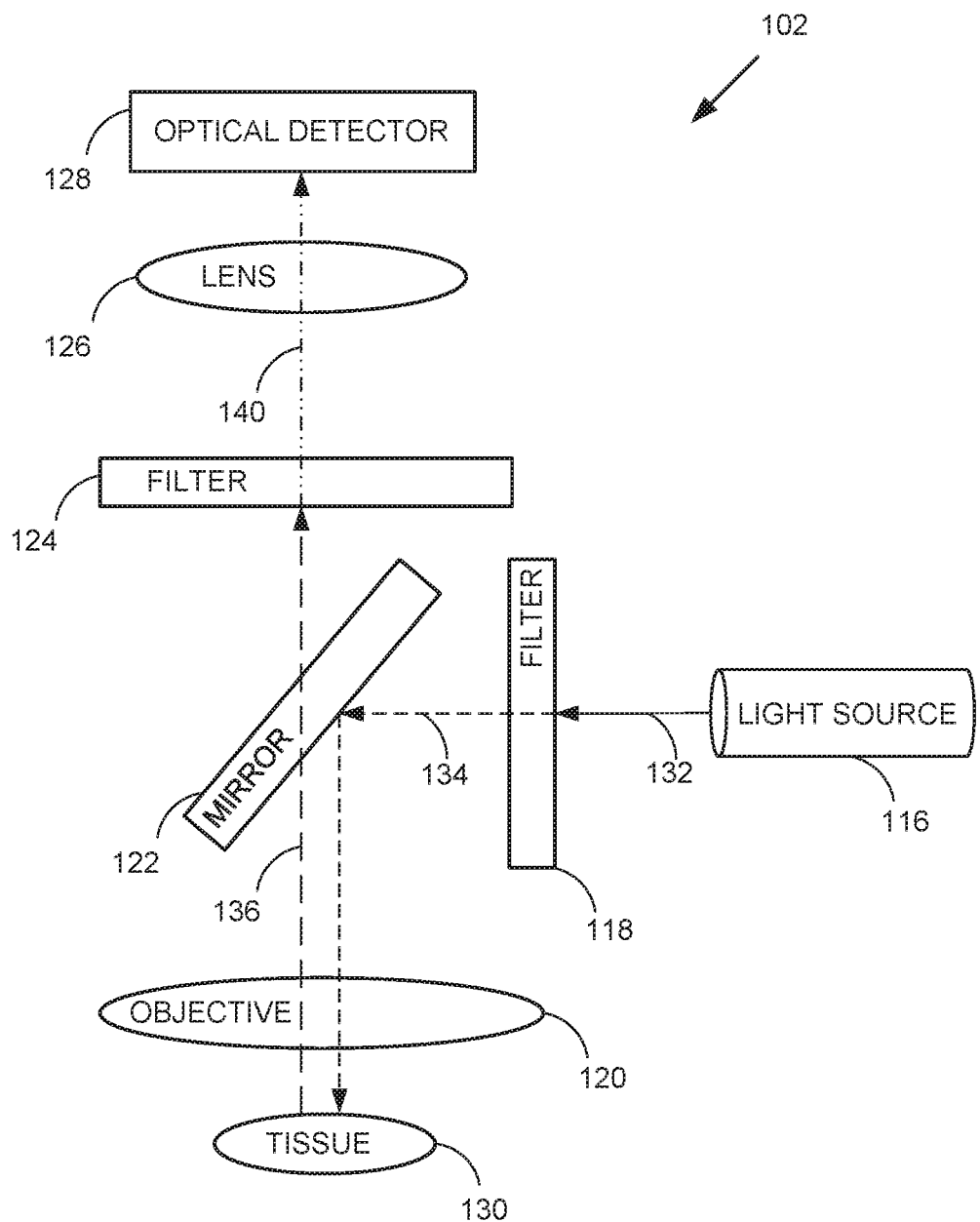

Reference is now made to FIGS. 1A-1B, which, taken together, are a schematic illustration of a fluorescent imaging device 100 operative to apply a limited variable gain for fluorescent imaging, in accordance with an embodiment of the disclosed technique. Fluorescent imaging device 100 includes at least a fluorescence camera 102, and a user interface (UI) 104, collectively references as imaging unit 106. Device 100 additionally includes a processing unit 108, an optional distance sensor 110, a memory unit 112, and a transceiver 114. Processing unit 108 may include any combination of a CPU, GPU, image processing unit, APU, digital signal processor (DSP), and the like. Transceiver 114 is operable to receive radio frequency (RF) signals relating to data and executable instructions. Transceiver 114 may be compatible with any communications protocols as are known in the art, such as WiFi, BlueTooth, and the like. Memory unit 112 is a non-transitory computer-readable storage medium operative to store computer code and data.

Each of imaging unit 106, distance sensor 110, transceiver 114, and memory unit 112 are coupled to processing unit 108. Additionally, at least UI 104 and fluorescent camera 102 are coupled to each other.

Memory unit 112 may store program code that is executable by processing unit 108 to perform one or more of the procedures described hereinbelow. Additionally, memory unit 112 may store multiple distance ranges in association with multiple gain values ranges. In one embodiment, any of the distance ranges, gain values and program code are received by device 100 via transceiver 114, and stored at memory unit 112 for subsequent use.

Referring to FIG. 1B, fluorescence camera 102 is configured to detect one or more fluorescent images of a tissue sample 130 labelled with fluorophores. Fluorescence camera 102 includes a light source 116, an excitation filter 118, an objective lens 120, a dichroic mirror 122, an emission filter 124, an imaging lens 126, and an optical detector 128. Optical detector 128 may by any of a CMOS or CCD camera.

Light source 116, excitation filter 118, dichroic mirror 122, and objective 120 are optically coupled for directing excitation light emitted by light source 116 onto tissue sample 130. Objective 120, dichroic mirror 122, emission filter 124, and imaging lens 126 are optically coupled for directing fluorescent light emitted by tissue sample 130 to optical detector 128. It may be noted that the optical setup of fluorescence camera 102 is intended as exemplary only, and other optical designs suitable for fluorescent imaging may be used. For example, in one embodiment, optical detector 128 and distance sensor 110 may be integrated within one optical detector, each comprising a separate optical channel.

Light source 116 is operative to emit a near-monochromatic light beam 132 including at least the excitation wavelengths corresponding to the wavelengths required to cause the fluorophores of tissue sample 130 to fluoresce. For example, if ICG is used to fluorescently label the tissue sample, the excitation wavelength may vary from 700 nanometers (nm) to 850 nm. Light source 116 is operative to direct near-monochromatic light beam 132 at excitation filter 118. Excitation filter 118 is operative to selectively transmit to dichroic mirror 122 the wavelengths of the emitted light 132 corresponding to the excitation wavelength of the fluorophores (i.e. 700-850 nm), as the excitation light beam 134. Dichroic mirror 122 is operative to direct the excitation light beam 134 to objective 120, which focuses excitation light beam 134 onto tissue sample 130.

The excitation light beam 134 is absorbed by the fluorophore labels of tissue sample 130, which then fluoresce. Tissue sample 130 emits an emission light beam 136 comprising the excitation wavelengths emitted by the fluorophores as well as additional reflected light, where the emitted fluorescent light has a different wavelength than the excitation light 134. Using the example above of using ICG labels, the excitation wavelengths may range from 750 nm to 900 nm. Objective 120 is operative to focus emission light beam 136 onto dichroic mirror 122, which directs emission light beam 136 to emission filter 124. Emission filter 124 is operative to selectively transmit the wavelengths of the emission light beam 136 as the excitation light 140 to optical detector 128 via imaging lens 126. Optical detector 128 is operative to detect at least one fluorescent image of tissue sample 130, by detecting excitation light 140 via an array of image pixels (not shown) as raw pixel values.

With reference to FIGS. 1A-1B, optical detector 128 is operative to provide the raw pixel values to processing unit 108. Processing unit 108 stores the raw pixel values at memory unit 112. The raw pixel values detected by detector 128 may suffer from attenuation due to the thickness of tissue sample 130, as well as due to the distance between tissue sample 130 and optical detector 128. To correct for the attenuation, processing unit 108 is operative to apply a limited variable-gain value to the raw pixel values to adjust the respective intensity values of the raw pixels, as follows:

Distance sensor 110 is operative to detect the distance between fluorescent imaging device 100 and tissue sample 130. In one embodiment, distance sensor 110 detects the distance between fluorescent imaging device 100 and tissue sample 130 optically. In this embodiment, distance sensor 110 includes a camera, and optionally a light source, such as an IR or near-IR laser. Distance sensor 110 may emit a light beam onto the tissue, and detect any of specular or diffuse reflectance off tissue sample 130. Processing unit 108 may analyze one or more properties of the reflectance to determine the distance between distance sensor 110 and tissue sample 130. Processing unit 108 may determine the distance between tissue sample 130 and optical detector 128 using the distance between distance sensor 110 and tissue sample 130 together with the internal geometry of fluorescent imaging device 100. For example, distance sensor 110 may be positioned at the distal end of fluorescent imaging device 100 in proximity to tissue sample 130, whereas, due to optical design considerations, optical detector 128 may be positioned proximally to distance sensor 110. Alternatively, optical detector 128 may be provided with two channels: a fluorescent channel to implement the fluorescent imaging, and a visible or NIR light channel implement distance sensor 110. Alternatively, distance sensor 110 may be implemented using other suitable techniques, such as ultrasound, RF and the like. Alternatively, distance sensor 110 may be implemented algorithmically, which will be described in greater detail below.

Processing unit 108 applies the distance determined above together with a limited variable gain algorithm to compute the gain with which to adjust the brightness of the raw pixel values within predefined brightness limits. The limited variable gain algorithm may associate each of a plurality of distance values with a respective predefined range of gain values, and that are collectively stored at memory unit 112. The limited variable gain algorithm may further impose an upper gain limit defined by the uppermost gain value of the highest range of gain values, and a lower gain limit defined by the lowermost gain value of the lowest range of gain values.

Processing unit 108 is operative to query the multiple distance values stored in memory unit 112 using the determined distance as a search query, and identify the associated range of gain values, accordingly. On finding a match, processing unit 108 is operative to apply an automatic gain controller (AGC) algorithm that determines which gain value within the gain values range to apply, by optimizing the brightness of the display image pixels subsequently displayed on UI 104 within the gain limits imposed by the matched gain values range. Processing unit 108 applies the gain value thus determined within the associated gain values range to the raw image pixels to derive the multiple display image pixels. Processing unit 108 may be additionally operative to apply one or more image processing techniques, as are known in the art, to process the gain adjusted pixel values to corresponding display pixel values, such as digital filters, image enhancers, and the like. Processing unit 108 stores the resulting display image pixel values in memory store 112. Processing unit is operative to communicate the display pixel values to UI 104. UI 104 is operative to display an image corresponding to the display image pixels, accordingly.

For example, the AGC algorithm may determine when to increase and decrease the applied gain within predefined gain limits until a pre-configured proportion of the image pixel values are within a target range. In one embodiment, the pre-configured proportion of image pixel values ranges between 70% and 95%, and the target pixel values range between 0 and 220 on a scale of 0 to 255.

In this manner, processing unit 108 applies the gain to compensate for the attenuation, while preventing background noise from being over-amplified. Using this technique, when blood tagged with the fluorescent dye is cleared from tissue sample 130, the upper gain limit imposes a ceiling on any gain increase for pixel values of images of tissue sample 130. As a result, when used for evaluating blood out-flow, the resulting gain-adjusted images are appropriately dimmed.

Figure 2:
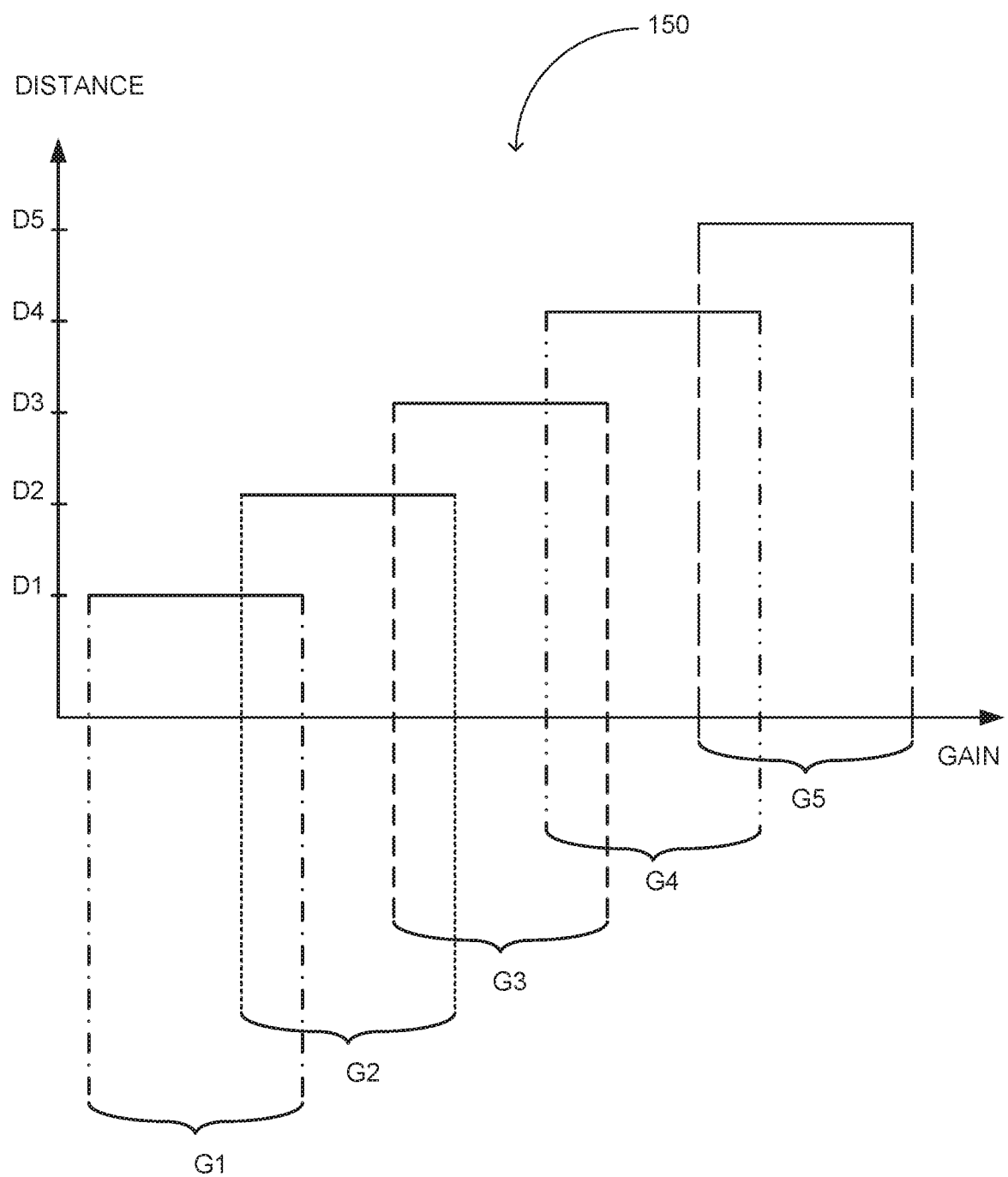
FIG. 2 illustrates a scheme for applying a limited variable gain to a fluorescent image, in accordance with an embodiment of the disclosed techniques.

Reference is now made to FIG. 2, which is a schematic illustration of an exemplary limited variable gain algorithm, generally referenced 150, for determining a corrective gain to adjust attenuated raw image pixels of a fluorescent image in accordance with another embodiment of the disclosed technique, and still referring to FIGS. 1A and 1B. Limited variable gain algorithm 150 may be employed by processing unit 108, to determine the appropriate gain to apply to the raw fluorescent image pixels acquired by optical detector 128. Exemplary variable gain algorithm 150 includes five different ranges of gain values: G1, G2, G3, G4, and G5, corresponding to five different distance values: D1, D2, D3, D4, D5, respectively. The ranges of the gain values G1, G2, G3, G4, and G5 are sequential and partially overlapping, i.e. a portion of each range of gain values overlaps with at least a portion of a previous range of gain values (previous overlapping range) or with a portion of a subsequent range of gain values (subsequent overlapping range). Distance value D1 corresponds to gain values range G1, and additionally with gain values range G2 in the subsequent overlapping region between G1 and G2. Distance value D2 corresponds to gain values range G2, and additionally with gain values range G1 in the previous overlapping region between G2 and G1, and with gain value G3 in the subsequent overlapping region between G2 and G3. Distance value D3 corresponds to gain values range G3, and additionally with gain values range G2 in the previous overlapping region between G3 and G2, and with gain values range G4 in the subsequent overlapping region between G3 and G4. Distance value D4 corresponds to gain values range G4, and additionally with gain values range G3 in the previous overlapping region between G4 and G3, and with gain values range G5 in the subsequent overlapping region between G4 and G5. Distance value D5 corresponds to gain values range G5, and additionally with gain values range G4 in the previous overlapping region between G5 and G4.

At time t, processing unit 108 determines the distance, d(t) between tissue sample 130 and optical detector 128. For example, processing unit 108 determines d(t) from a distance measurement acquired by distance sensor 110. Processing unit 108 queries memory unit 112 with d(t) to identify one of the distance values D1-D5 that matches d(t). When finding the match, processing unit 108 obtains the gain value range, (i.e., one of G1-G5) associated with the matched distance value, and applies a gain within the range to the raw pixel values using the AGC algorithm. If d(t) corresponds to one of the overlapping regions, and thus corresponds to two different gain value ranges, processing unit 108 may employ a smoothing technique to determine which of the gain value ranges to apply, and thereby prevent jumping between the different gain value ranges.

One possible smoothing technique may be to impose a path dependency on the limited variable gain algorithm as distance changes with time: on determining that the distance d(t) falls within a current gain values range, an upwards distance threshold may be imposed while distance is increasing, and a downwards threshold may be imposed while distance is decreasing to maintain a steady gain value range.

The following is an exemplary implementation of such a smoothing technique. Beginning at time $t_0$, processing unit 108 uses the distance is increasing, and a downwards threshold may be imposed while distance is decreasing to maintain a steady gain value range.

The following is an exemplary implementation of such a smoothing technique. Beginning at time $t_0$, processing unit 108 uses the distance detected by sensor 110 to determine the distance $d(t_0)$ between tissue sample 130 and optical detector 128. Processing unit determines that $d(t_0)$ corresponds to gain values range G2. Processing unit 108 applies a gain from the values range G2 to the raw image pixels, and displays an image described by the gain adjusted pixels, accordingly.

At time $t_1$, the distance between fluorescent imaging device 100 and tissue sample 130 increases, i.e. $d'(t_1)>0$. Processing unit 108 employs the distance detected by sensor 110 at time $t_1$ to determine the distance $d(t_1)$ between tissue sample 130 and optical detector 128. Processing unit determines that $d(t_1)$ has not yet reached the predefined upwards threshold of D2: thus, $d(t_1)<UPPERBOUND_{D2}$ and the applied gain at $t_1$ remains within values range G2. Processing unit 108 applies a gain value from the values range G2 to the raw image pixels, and displays an image described by the gain adjusted pixels, accordingly.

At time $t_2$, the distance between fluorescent imaging device 100 and tissue sample 130 continues to increase, i.e. $d'(t_2)>0$. Processing unit 108 employs the distance detected by sensor 110 at time $t_2$ to determine the distance $d(t_2)$ between tissue sample 130 and optical detector 128. Processing unit 108 determines that $d(t_2)$ exceeds the predefined upper-bound threshold, i.e. $d(t_2)>UPPERBOUND_{D2}$ and thus the distance is categorized as D3. As a result, processing unit 108 increases the gain values range to G3. Processing unit 108 applies a gain value from the gain values range G3 to the raw image pixels, and displays an image described by the gain adjusted pixels, accordingly.

At time $t_3$, the distance between fluorescent imaging device 100 and tissue sample 130 begins to decrease: i.e. $d'(t_3)<0$. Processing unit 108 employs the distance detected by sensor 110 at time $t_3$ to determine the distance $d(t_3)$ between tissue sample 130 and optical detector 128. Processing unit 108 determines that $d(t_3)$ has decreased below $UPPERBOUND_{D2}$, but has not yet reach the predefined lower-bound threshold $LOWERBOUND_{D3}$, where $LOWERBOUND_{D3}<UPPERBOUND_{D2}$. Processing unit 108 applies a gain value from the gain values range G3 to the raw pixel values, and displays an image described by the gain adjusted pixels, accordingly.

At time $t_4$, the distance between fluorescent imaging device 100 and tissue sample 130 continues to decrease: i.e. $d'(t_4)<0$. Processing unit 108 employs the distance detected by sensor 110 at time $t_4$ to determine the distance $d(t_4)$ between tissue sample 130 and optical detector 128. Processing unit 108 determines that $d(t_4)$ crosses the lower-bound threshold $LOWERBOUND_{D3}$. As a result, processing unit 108 reduces the gain values range to G2, applies a gain value from the gain values range G2 to the raw pixel values, and displays an image described by the gain adjusted pixels, accordingly.

Another possible technique for prevent oscillation between different gain levels in the respective overlapping distance regions is to define impose a path dependency, or hysteresis loop, on the limited variable gain algorithm. Thus, the algorithm may impose different distance threshold values for increasing and decreasing the respective gain value. For example, within the subsequent overlapping region between ranges D2 and D3, a ramp-up distance $D2_{ramp-up}$ may define the point at which the gain values range is increased from G2 to G3. Thus, while the distance between fluorescent imaging device 100 and tissue sample 130 remains less than $D2_{ramp-up}$ the applied gain value is selected from gain values range G2. When the distance between fluorescent imaging device 100 and tissue sample 130 is increased to reach $D2_{ramp-up}$, the respective gain values range is increased from G2 to G3, and the applied gain value is selected from range G3, accordingly. Similarly, within the previous overlapping region between ranges D3 and D2, a ramp-down distance $D3_{ramp-down}$ may define the point at which the gain values range decreases from G3 to G2, where $D3_{ramp-down} < D2_{ramp-up}$. Thus, while the distance between fluorescent imaging device 100 and tissue sample 130 remains greater than $D3_{ramp-down}$ the applied gain value is selected from gain values range G3. When the distance between fluorescent imaging device 100 and tissue sample 130 is decreased to below $D3_{ramp-down}$ the applied gain value is selected gain values range G2. Such a scheme of ramp-up and ramp-down distances may be applied to each of the overlapping regions, imposing a path-dependent loop for varying the applied gain according to measured distance.

In general, it may be noted that by predefining minimum and maximum gain values of G1 and G5, the risk of applying too much, or too little gain to the raw pixel values is reduced, thereby reducing the risk of producing over-saturated fluorescent images or under-saturated fluorescent images.

In one implementation, distance sensor 110 may be software-implemented by processing unit 108. Processing unit 108 may determine the gain as a function of the software processing of the raw pixel values detected by detector 128. In this implementation, the limited variable gain algorithm may be expressed as a function F defining the intensity of a display pixel value of pixel p at time t, $I_p(p, t)$ in terms of one or more of: the intensity of the fluorescent light at time t $I_f(t)$; the intensity of the excitation light at time t $I_i(t)$; the distance at time t d(t) between optical detector 128 and tissue sample 130; and the applied gain value at time t, g(t) as follows:

$$I_p(p,t)=F(I_f(t),I_i(t),d(t),g(t)) \quad (1)$$

If F is an invertible function, i.e. $F^{-1}$ is driven by measuring the excitation light reflected from the tissue via an additional sensor (not shown), any given time t, under a known applied gain value g(t), processing unit 108 may determine the distance d(t) from measured values for the intensity of the fluorescent light; the intensity of the excitation light; and the intensity of a display pixel value of pixel p, respectively, i.e. $I_f(t)$, $I_i(t)$, and $I_p(p, t)$:

$$d(t)=F^{-1}(I_f(t),I_i(t),I_p(p,t),g(t)) \quad (2)$$

In this manner, processing unit 108 may apply varying gain values to determine the association between the distance range and gain. Subsequently, processing unit 108 may apply this association to the technique described above with reference to FIGS. 1A-1B and 2.

In another software implementation, processing unit 108 may determine the distance empirically as follows. Initially processing unit 108 selects several candidate gain values from several ranges, i.e. G2, G3, and G4. Processing unit 108 applies these candidate gain values to the raw image pixels. Processing unit 108 evaluates the image quality resulting from the applied candidate gain values, and selects the candidate gain value corresponding to the best image quality. For example, processing unit 108 may determine that images adjusted with a gain within range G2 are under-saturated, and images adjusted with a gain from range G4 are over-saturated, and that the optimal gain adjustment is from range G3, corresponding to a distance of D3. In this manner, processing unit 108 may apply varying gain values to determine the association between the distance range and gain.

In one embodiment, the user may slightly adjust the distance between fluorescent imaging device 100 and tissue sample 130 while applying the gain from range G3. Processing unit 108 may determine the distance within the range D3 that corresponds to the optimal image quality under gain adjustment from range G3. Processor 108 may set this distance as a calibration distance $d_{cal}(t)$. In a similar manner, processor 108 may determine the upper-bound and lower-bound thresholds for D3, $UPPERBOUND_{D3}$ and $LOWERBOUND_{D3}$, by evaluating the image quality along the distance range D3. In a similar manner, processor 108 may define the upper-bound and lower-bound thresholds for the remaining distance ranges. It may be noted that processing unit 108 may determine the gain using any combination of the above techniques for example, by receiving a set of gain values associated with a set of distance ranges via transceiver 114, and fine-tuning any of the distance ranges and gain values by applying any combination of the software techniques described hereinabove.

Figure 3:
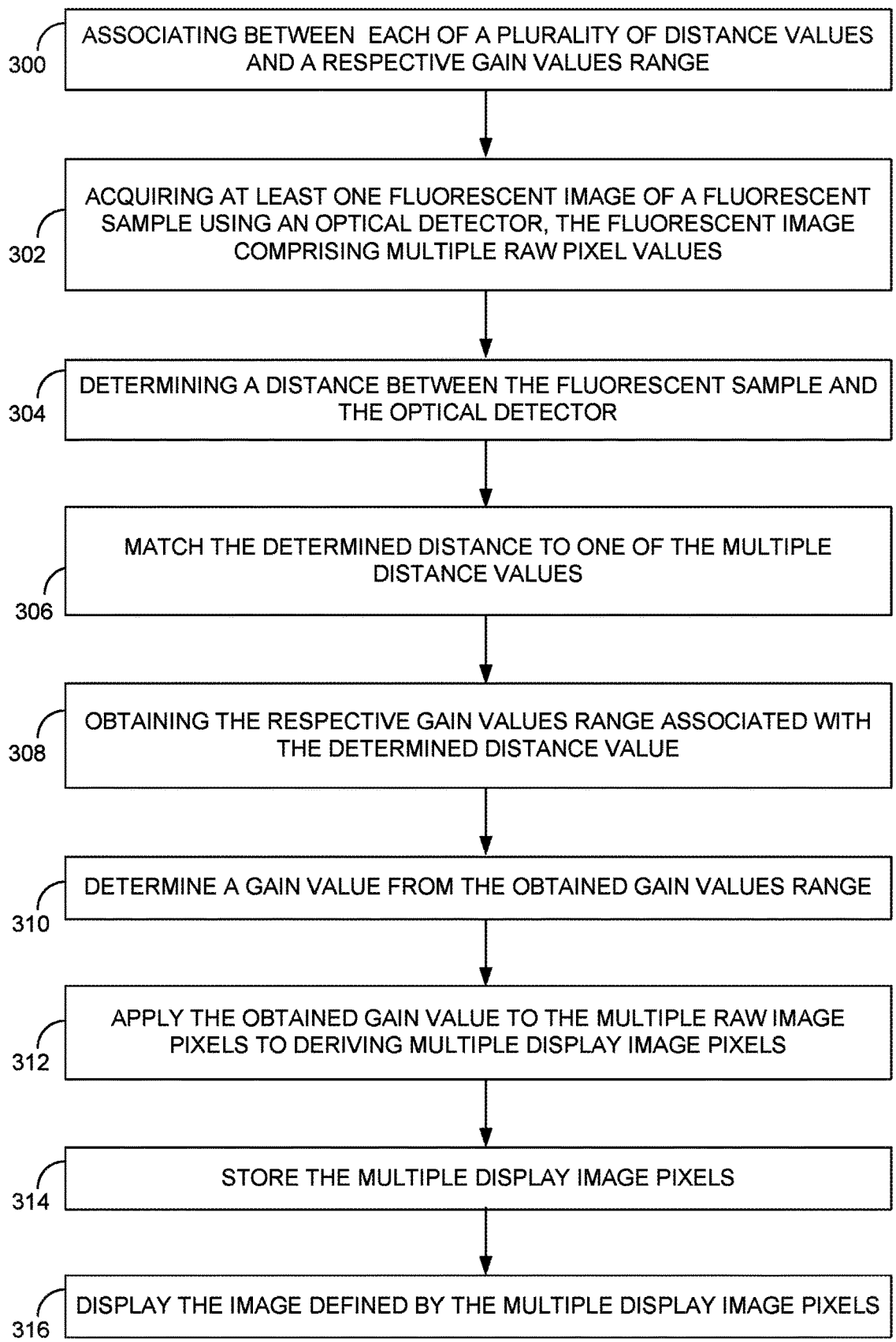
FIG. 3 is a schematic illustration of a method for applying a limited variable gain to a fluorescent image, in accordance with an embodiment of the disclosed techniques.

A description of a method for applying a limited variable gain to a fluorescent image now follows. Reference is now made to FIG. 3, which is a schematic illustration of a method for applying a limited variable gain to multiple raw image pixels of a fluorescent tissue sample, in accordance with a further embodiment of the disclosed technique.

In procedure 300, each of a plurality of distance values is associated with a respective gain values range. With reference to the system of FIGS. 1A-1B, processing unit 108 associates each of a plurality of distance values with a respective gain value range. In one embodiment, each of the plurality of distance values are stored in association with each respective gain values range in memory unit 112, and subsequently accessed by processing unit 108. The plurality of gain values ranges are sequential and may be partially overlapping. For example, each one of the plurality of gain values ranges may partially overlap with at least a portion of a previous one or a subsequent one of the plurality of gain values ranges. When a first gain values range overlaps with a portion of a previous gain values range, the overlapping region therebetween is denoted as a previous overlapping region of the respective first gain values range. Similarly, when a second gain values range overlaps with a portion of a subsequent gain values range, the overlapping region therebetween is denoted as a subsequent overlapping region of the respective second gain values range.

In procedure 302, at least one fluorescent image of a fluorescing sample is acquired by an optical detector, the at least one fluorescent image comprising of multiple raw pixel values.

In procedure 304, the distance between the optical detector and the fluorescing sample is determined. With reference to the system of FIGS. 1A-1B, distance sensor 110 measures the distance between distance sensor 110 and the fluorescent tissue sample 130. Processing unit 108 determines the distance between optical detector 128 and fluorescent tissue sample 130 by applying the measured distance between distance sensor 110 and the fluorescent tissue sample 130 together with the internal geometric configuration of distance sensor 110 and optical detector 128 within device 100.

In procedure 306, the determined distance is matched to one of the plurality of distance values, each distance value stored in association with one of the respective gain value ranges.

In procedure 308, the gain values range associated with the determined distance value is obtained.

In procedure 310, a gain value from the obtained gain values range associated with the determined distance, is determined.

With reference to the system of FIG. 2, and still referring to the system of FIGS. 1A-1B, processing unit 108 matches the determined distance to one of the plurality of distance values stored in association with the multiple gain value ranges at memory unit 112. Processing unit 108 obtains from memory unit 112 the gain values range stored in association with the distance value that matched the determined distance. Processing unit 108 applies an AGC algorithm to the fluorescent image acquired by optical detector 128 to determine when to increase and when to decrease the applied gain within predefined gain limits. Processing unit 108 may determine to adjust the gain on the raw pixel values until a pre-configured proportion of the image pixel values of the acquired image are within a target range. The pre-configured proportion of image pixel values may range from 70% to 95%, and the target pixel values may range between 0 and 220 on a scale of 0 to 255. In another embodiment, processing unit 108 may employ a smoothing technique to select which of multiple gain value ranges, each associated with the determined distance value, to apply, and thereby prevent jumping between two different gain value ranges. In yet a further embodiment, processing unit 108 imposes a path dependent hysteresis loop as a smoothing function on the applied gain values.

In procedure 312, the gain value is applied to the multiple raw image pixels.

In procedure 314, the multiple display image pixels are stored.

In procedure 316, an image defined by the multiple display image pixels is displayed.

With reference to the system of FIG. 2, and still referring to the system of FIGS. 1A-1B, processing unit 108 applies the determined gain value within the gain values range to the raw pixel values, accordingly, to derive multiple display pixel values defining a fluorescent image. Processor 108 may apply additional image processing techniques to the display image pixels as are known in the art, such as to, digital filters, enhancers, smoothing algorithms, and the like. Processing unit 108 stores the multiple raw pixel values at memory unit 112. Processing unit 108 provides the multiple display image pixels to user interface 104, which displays the fluorescent image defined by the multiple display image pixels, accordingly.

It will be appreciated by persons skilled in the art that the disclosed technique is not limited to what has been particularly shown and described hereinabove. Rather the scope of the disclosed technique is defined only by the claims, which follow.

What is claimed is:

1. A fluorescent imaging device, comprising:
a fluorescent camera comprising an optical detector that is configured to acquire at least one fluorescent image of a fluorescing sample, wherein said at least one fluorescent image comprises multiple raw image pixels;
a user interface configured to display an image formed from multiple display image pixels, said multiple display image pixels derived from said multiple raw image pixels;
a distance sensor configured to measure a distance to said fluorescing sample and provide said measured distance; and
at least one hardware processor configured to:
determine from said measured distance a distance between said optical detector and said fluorescing sample,
access a predetermined mapping between a plurality of distance values and a plurality of gain values ranges, wherein larger distance values in the plurality of distance values are mapped to higher gain value ranges in the plurality of gain values ranges, and smaller distance values in the plurality of distance values are mapped to lower gain values ranges in the plurality of gain value ranges,
match said determined distance to one distance value among the plurality of distance values, the match using a ramping smoothing technique in a case the determined distance falls in overlapping regions corresponding to different gain values ranges,
obtain one gain values range among the plurality of the gain values ranges corresponding to said matched one distance value based on the predetermined mapping,
obtain a gain value, selected from the one gain values range, wherein limits of the one gain values range are applied to limit said gain value,
apply said gain value to said multiple raw image pixels to derive said multiple display image pixels, and
cause said multiple display image pixels to be provided to said user interface.

2. The fluorescent imaging device of claim 1, further comprising a memory configured to store said predetermined mapping between said plurality of distance values and said plurality of gain values ranges.

3. The fluorescent imaging device of claim 1, wherein each distance value of the plurality of distance values is a discrete distance value, and wherein each gain values range of the plurality of gain values ranges is a different range from every other gain values range of the plurality of gain values ranges.

4. The fluorescent imaging device of claim 3, wherein the predetermined mapping includes a one-to-one mapping between the discrete distance values and the different gain values ranges.

5. The fluorescent imaging device of claim 1, wherein at least two gain values ranges of the plurality of gain values ranges overlap each other.

6. The fluorescent imaging device of claim 1, wherein the ramping smoothing technique applies a hysteresis loop.

7. The fluorescent imaging device of claim 1, wherein:
the distance sensor is configured to measure a second measured distance,
the at least one hardware processor is further configured to determine from the second measured distance a second distance between the optical detector and the fluorescing sample,
the plurality of distance values includes at least a first distance value and a second distance value greater than the first distance value, and
the plurality of gain values ranges includes at least a first gain values range corresponding to the first distance value and a second gain values range corresponding to the second distance value, wherein at least a portion of the second gain values is higher than the first gain values range.

8. The fluorescent imaging device of claim 7, wherein the ramping smoothing technique applies a ramping-up region above the first distance value and a ramping-down region below the second distance value, wherein an upper bound of the ramping-up region above the first distance value is above a lower bound of the ramping-down region below the second distance value.

9. The fluorescent imaging device of claim 8, wherein the one distance value matched to the determined distance is the first distance value, and
wherein the at least one hardware processor is further configured to apply the ramping smoothing technique to:
in case the determined second distance is within the ramping-up region above the first distance value, match the determined second distance to the first distance value, and
in case the determined second distance is above the ramping-up region above the first distance value, match the determined second distance to the second distance value.

10. The fluorescent imaging device of claim 9, wherein:
the second distance value matched to the determined second distance is the second distance value,
the distance sensor is configured to measure a third measured distance, and
the at least one hardware processor is further configured to:
determine from the third measured distance a third distance between the optical detector and the fluorescing sample, and
apply the ramping smoothing technique to:
in case the determined third distance is within the ramping-down region below the second distance value, match the determined third distance to the second distance value, and
in case the determined third distance is below the ramping-down region below the second distance value, match the determined third distance to the first distance value.

11. A method for applying a variable gain to a fluorescent image, comprising:
acquiring, by an optical detector comprising a camera, at least one fluorescent image of a fluorescing sample, wherein said at least one fluorescent image comprises multiple raw image pixels;
determining, by a distance sensor, a distance between said optical detector and said fluorescing sample;
accessing a predetermined mapping between a plurality of distance values and a plurality of gain values ranges, wherein larger distance values in the plurality of distance values are mapped to higher gain value ranges in the plurality of gain values ranges, and smaller distance values in the plurality of distance values are mapped to lower gain values ranges in the plurality of gain value ranges;
matching, by a processor, said determined distance to one distance value among said plurality of distance values, the matching using a ramping smoothing technique in a case the determined distance falls in overlapping regions corresponding to different gain values ranges;
obtaining, by the processor, one gain values range among the plurality of the gain values ranges corresponding to said matched one distance value based on the predetermined mapping;
obtaining, by the processor, a gain value, selected from the one gain values range, wherein limits of the one gain values range are applied to limit said gain value;
applying said gain value to said multiple raw image pixels to derive multiple display image pixels; and
storing said multiple display image pixels.

12. The method of claim 11, further comprising measuring a distance from said fluorescing sample, and applying said measured distance to determine said distance between said optical detector and said fluorescing sample.

13. The method of claim 11, wherein each distance value of the plurality of distance values is a discrete distance value, and wherein each gain values range of the plurality of gain values ranges is a different range from every other gain values range of the plurality of gain values ranges.

14. The method of claim 13, wherein the predetermined mapping includes a one-to-one mapping between the discrete distance values and the different gain values ranges.

15. The method of claim 11, wherein the ramping smoothing technique applies a hysteresis loop.

16. A non-transitory computer-readable storage medium having program code embodied thereon which, when executed by at least one hardware processor, causes performance of a method comprising:
accessing at least one fluorescent image of a fluorescing sample, acquired by an optical detector comprising a camera, wherein said at least one fluorescent image comprises multiple raw image pixels;
accessing a determined distance between the optical detector and the fluorescing sample;
accessing a predetermined mapping between a plurality of distance values and a plurality of gain values ranges, wherein larger distance values in the plurality of distance values are mapped to higher gain value ranges in the plurality of gain values ranges, and smaller distance values in the plurality of distance values are mapped to lower gain values ranges in the plurality of gain value ranges;
matching said determined distance to one distance value among the plurality of distance values, the matching using a ramping smoothing technique in a case the determined distance falls in overlapping regions corresponding to different gain values ranges;
obtaining one gain values range among the plurality of the gain values ranges corresponding to said matched one distance value based on the predetermined mapping;
obtaining a gain value, selected from the one gain values range, wherein limits of the one gain values range are applied to limit said gain value;
applying said gain value to said multiple raw image pixels to derive multiple display image pixels, said multiple display image pixels forming an image; and
storing said multiple display image pixels.

17. The non-transitory computer-readable storage medium of claim 16, wherein said program code is further executable to apply a measured distance from said fluorescing sample to determine said distance between said optical detector and said fluorescing sample.

18. The non-transitory computer-readable storage medium of claim 16, wherein each distance value of the plurality of distance values is a discrete distance value, and wherein each gain values range of the plurality of gain values ranges is a different range from every other gain values range of the plurality of gain values ranges.

19. The non-transitory computer-readable storage medium of claim 18, wherein the predetermined mapping includes a one-to-one mapping between the discrete distance values and the different gain values ranges.

20. The non-transitory computer-readable storage medium of claim 16, wherein the ramping smoothing technique applies a hysteresis loop.

* * * * *